United States Patent [19]

Carta et al.

[11] Patent Number: 5,420,024
[45] Date of Patent: May 30, 1995

[54] **PROCESS FOR SYNTHESIS OF ACYLATED HMG-COA REDUCTASE INHIBITORS FROM A LACTONE DIOL PRECURSOR USING *CANDIDA CYLINDRACEA***

[75] Inventors: Giorgio Carta, Charlottesville; Michael J. Conder, Harrisonburg; John L. Gainer, Charlottesville; Robert W. Stieber, Harrisonburg; Victor A. Vinci, Charlottesville, all of Va.; Timothy W. Weber, Grampian, Pa.

[73] Assignees: Merck & Co., Inc., Rahway, N.J.; The University of Virginia Alumni Patents Foundation, Charlottesville, Va.

[21] Appl. No.: 60,847

[22] Filed: May 11, 1993

[51] Int. Cl.⁶ ............................................. C12P 17/06
[52] U.S. Cl. ................................... 435/125; 425/280; 425/921
[58] Field of Search ............................... 435/280, 125

[56] References Cited

U.S. PATENT DOCUMENTS 5,223,415 6/1993 Conder et al. ................. 435/125

FOREIGN PATENT DOCUMENTS 60-176595 9/1985 Japan .

OTHER PUBLICATIONS

Hills M J et al, BBA 1042:237–240 (1990).
Okamura S et al, BBA 575:156–165 (1979).
Jones J B, Tetrahedron 42:3351–3403 (1986).
Wang Y-F et al, J. Am. Chem. Soc. 110:7200–05 (1988).
Landrand G, Tetrahedron Letts 27:29–32 (1986).
Komagata D, J. Ant. Biot 39:1574–7 (1986).

*Primary Examiner*—Irene Marx
*Assistant Examiner*—S. Saucier
*Attorney, Agent, or Firm*—Carol S. Quagliato; Catherine A. Dolan; Melvin Winokur

[57] ABSTRACT

An immobilized lipase is employed in an organic solvent to esterify diol lactone derivatives of HMG-CoA reductase inhibitors to form HMG-CoA reductase inhibitors of formula (I).

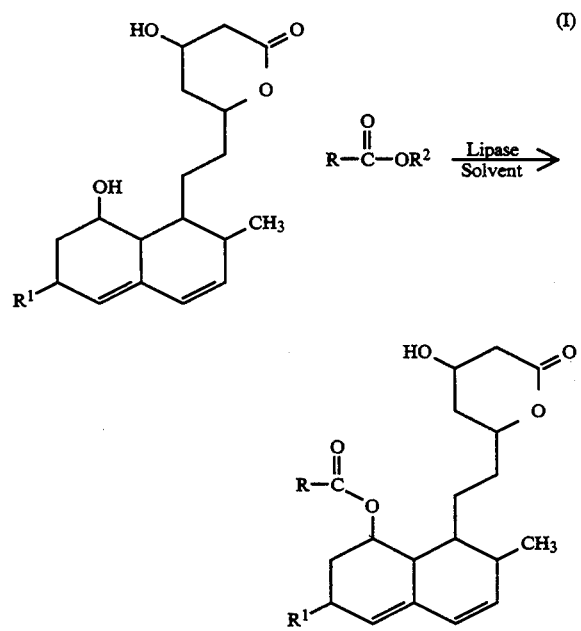

This process allows for the efficient, one-step production of HMG-CoA reductase inhibitors of structural formula (I).

7 Claims, No Drawings

PROCESS FOR SYNTHESIS OF ACYLATED HMG-COA REDUCTASE INHIBITORS FROM A LACTONE DIOL PRECURSOR USING CANDIDA CYLINDRACEA

BACKGROUND OF THE INVENTION

HMG-CoA reductase inhibitors containing a polyhydronaphthyl group as the hydrophobic moiety may be prepared by a multi-step chemical synthesis from the diol lactone which has previously been blocked at the lactone hydroxyl with a silyloxy protecting group or in some cases these compounds may be prepared by chemical modification of the natural products mevastatin and lovastatin. Mevastatin and lovastatin are prepared by a biosynthetic fermentation process.

It would be highly advantageous to have a one step efficient process which could be employed to prepare HMG-CoA reductase inhibitors, such as lovastatin, from the available diol lactone.

DESCRIPTION OF THE INVENTION

This invention relates to an esterification process for forming HMG-CoA reductase inhibitors of formula (I):

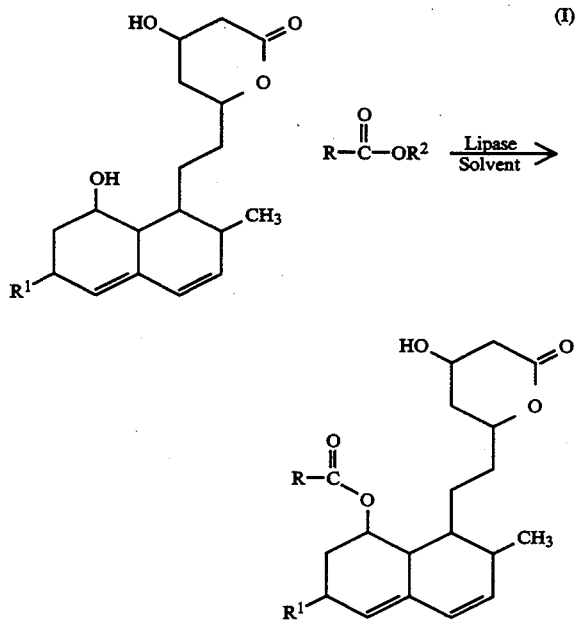

wherein
R is $C_{1-5}$alkyl;
$R^1$ is H, $CH_3$, or OH;
$R^2$ is H or $C_{1-5}$alkyl.

More specifically the process employs an immobilized lipase enzyme in a nonaqueous organic solvent. The source of the lipase enzyme may be selected from the group listed in Table I; the organisms listed therein have been shown to produce enzymes capable of deacylating lovastatin to triol acid (EP 486,153, published May 20, 1992). This list is not intended to be exhaustive and should be understood to include other organisms that produce enzymes which catalyze the side-chain removal of lovastatin and compactin. The process of the present invention employs, preferably, an immobilized enzyme (lipase or esterase); a specific example of a suitable immobilization procedure for use with a commercially available enzyme is given in Example 1 and further discussed below. Other methods for obtaining immobilized enzyme include growing up the producing organism in a suitable nutrient medium, harvesting the microbial cells and lyophilizing them; this illustrates the simplest form of immobilization, however, such a method has the potential drawbacks of the enzyme not having been purified in any way, thereby making the specific activity of the preparation lower than when a more purified preparation is employed, and the presence of the microbial cell wall which may act as a permeability barrier to the reactants (substrate). More preferable methods utilize enzymes which have been released from microbial cells (through mechanical or enzymatic breakage) and purified to some extent. The means by which proteins (enzymes) can be purified from complex biological mixtures are well known to those skilled in the art and include centrifugation, ultrafiltration, salting out (with e.g. ammonium sulfate), various types of column chromatography (ion-exchange, hydrophobic interaction, gel filtration and affinity) and electrophoresis. The purification of the desired enzyme can be conveniently monitored throughout the purification process by assaying putative enzyme-containing fractions from the various purification steps for the ability to hydrolyze the side chain from lovastatin acid (which can be carded out in aqueous solution and monitored via HPLC analysis). The choice of immobilization support useful for the attachment of the enzyme is not confined to nylon (as used in the Example given) but may be any other support used by the skilled artisan for enzyme immobilization; examples include polyacrylamide, agarose and other commercially available, activated support resins such as Emphase TM (3M Corp.) and Eupergit® C (Rohm Pharma). It is possible that some organisms may produce extracellular forms of lipase or esterase; purification of such enzymes can also be accomplished using the methods discussed above, however, the step of releasing the enzyme from the producing cells would not be necessary in this case.

A particular example of such a lipase enzyme is Candida cylindracea C (Type VII from the Sigma Chemical Co). The lipase enzyme is conveniently immobilized on nylon 6 pellets employing the procedure of Example 1. The nonaqueous organic solvent may be selected from any organic solvent capable of dissolving the stated diol lactone without deactivating the enzyme. Particular examples of such solvents include mixtures of a chlorinated hydrocarbon such as chloroform or methylene chloride and a hydrocarbon such as hexane or toluene. Specifically illustrating such a mixture is a 50/50 mixture of chloroform and hexane. The reaction may take place between stoichiometric proportions of acid or ester and diol lactone or excesses of the acid or ester may be used. The temperature employed may be 15°–40° C. with a preferred range being 20°–37° C.

Compounds of formula (I) which may be prepared include those wherein R is ethyl, n-propyl, 2-butyl or 2-methyl-2-butyl. The starting lactones have been previously reported in the literature and their preparation is known to those skilled in the art. The starting carboxylic acids and their corresponding esters are all commercially available. The lipase enzymes are either available from commercial sources or the microbes which make the enzyme have been deposited with the ATCC and available from that source.

TABLE 1

| strain name | ATCC No. |
|---|---|
| *Mortierella isabellina* | 42013 |
| *Mucor circinelloides* | 1207a |
| *Fusarium solani* | 12826 |
| *Dechotomomyces cejpii* | 22149 |
| *Dechotomomyces cejpii* | 42284 |
| *Diheterospora chlamydosporia* | 16449 |
| *Diheterospora chlamydosporia* | 18056 |
| *Diheterospora chlamydosporia* | 20537 |
| *Emericella unguis* | 10073 |
| *Emericella unguis* | 12063 |
| *Emericella unguis* | 13431 |
| *Emericella unguis* | 16812 |
| *Humicola fuscoatra* | 12774 |
| *Humicola fuscoatra* | 52037 |
| *Humicola fuscoatra* | 62175 |
| *Mortierella isabellina* | 36670 |
| *Mortierella isabellina* | 38063 |
| *Mortierella isabellina* | 44853 |
| *Neocosmospora africana* | 24342 |
| *Xylogone sphaerospora* | 42027 |
| *Penicillium chrysogenum* | 10002 |
| *Aspergillus clavatus* | 1007 |
| *Gilmaniella humicola* | 16013 |
| *Mucor bainieri* | 42642 |
| *Chaetomium cochliodes* | 10195 |
| *Clonostachys compactiuscula* | 38009 |
| *Candida cylindracea* (Sigma Chemical Co.) | 74178 |

EXAMPLE 1

Procedure For Enzyme Immobilization

1. Approximately 10 g of Nylon 6 pellets, previously frozen and ground to between 425 and 1180 gm, was weighed out.
2. A pH 7 phosphate buffer was prepared by adding $Na_2HPO_4 \cdot 7H_2O$ to deionized water to obtain pH $9.0 \pm 0.5$ followed by addition of 1N HCl to bring the pH to 7.0.
3. A 2.5% glutaraldehyde solution was prepared by adding to 10 ml of a 25% solution enough pH 7 phosphate buffer to make 100 ml.
4. 6N HCl was added to the nylon pellets in a beaker and stirred constantly for 10–15 seconds. The acid was decanted and the pellets rinsed with deionized water until clear; a spatula was used to break up Imps of hydrolyzed nylon.
5. The nylon was filtered on a buchner funnel to achieve dryness.
6. The dried nylon clumps were broken up in a mortar and pestle and then transferred to a flask with 100 ml of the 2.5% glutaraldehyde solution. The mixture was stirred for at least 1 hour.
7. The enzyme attachment solution was prepared by mixing 4.8 g of lipase in 30 ml of the pH 7 phosphate buffer in a 50 cc culture tube. The mixture was shaken to get as much lipase into solution as possible.
8. The previously stirred nylon glutaraldehyde solution was decanted and the nylon washed with 100 ml of deionized water and then again with 500 ml of deionized water. The nylon was filtered and dried.
9. A portion of the enzyme attachment solution (0.5 ml) was drawn for protein analysis and the nylon pellets were added to the enzyme attachment solution. The bottle was rolled for 18–24 hours and a Second aliquot was removed for protein analysis.
10. The attachment solution was decanted and the nylon washed with deionized water. The nylon was spread out and allowed to dry overnight.

EXAMPLE 2

Isolation and Extraction of Diol Lactone

Wherein R 1 is methyl a. Triol Workup

The triol acid corresponding to the diol lactone was prepared according to the procedure in EPO publication 517,413 published Dec. 19, 1992. Ammonium sulfate was added to the fermentation broth in an amount sufficient to bring the concentration to 0.25M. Isopropyl acetate was added in volume equal to $0.8 \times$ the fermentation broth followed by the addition of isopropyl alcohol in equal volume to $0.05 \times$ the isopropyl acetate volume. The broth was adjusted to pH 4.0 with 2N $H_2SO_4$ and then agitated for 30 minutes, centrifuged and the upper isopropyl acetate layer recovered.

b. Carbonate extraction

Dilute carbonate solution (25 g/l $Na_2CO_3$) was added to the isopropyl acetate solution in volume equal to $0.4 \times$ the isopropyl acetate. The resulting solution was agitated for 30 minutes, centrifuged and the upper isopropyl acetate and lower carbonate aqueous layer separated.

c. Second isopropyl acetate extraction

An equal volume of isopropyl acetate was added to the carbonate solution. The pH was adjusted to 4.0 with 85% $H_3PO_4$ and the solution agitated for 30 minutes! centrifuged and the upper isopropyl acetate layer recovered.

d. Lactonization

70% methanesulfonic acid was added to the recovered isopropyl acetate solutions to achieve a final concentration of 10 mM. The resulting mixture was evaporated in vacuo at 33°–34° C. to 20% of the original volume.

e. Dilute Carbonate Wash

The lactonized solution from step (d) was added to a separatory funnel and cold, dilute carbonate was added in an equal volume to isopropyl acetate. The mixture was agitated for 1–2 minutes over ice and the upper isopropyl acetate layer was recovered.

f. Crystallization

The covered solution from step (e) was stored in a freezer while crystals were formed. The crystals were filtered and the excess isopropyl acetate was collected. The crystals were washed with cold toluene/isopropyl acetate (9:1) until the wash was clear and the crystals vacuum dried at room temperature.

EXAMPLE 3

Enzymatic Acylation of Diol Lactone Formation of Lovastatin

A reaction mixture containing the following components was prepared.

| | |
|---|---|
| Lovastatin Diol Lactone | 50.5 mg |
| 2-methylbutyric acid | 452 µl |

| | | |
|---|---|---|
| -continued | | |
| Chloroform | 5.0 ml | |
| hexane | 5.0 ml | |
| Nylon Immmob. Enzyme | 1.0 g | |

The 10 ml reaction mixture was incubated in a screw-capped test tube and placed on a Rotator equipped with a disc containing test tube holders. The reactions were carded out at 25° C. or 37° C. for 2 to 24 hours with sample taken at regular intervals. Lovastatin was detected by HPLC. Lovastatin separation was on a $C_{18}$ reverse phase column using an eluent of 50% acetonitrile and 50% $H_3PO_4$ in $H_2O$ at a flow rate of 3 ml/min. Detection was at 238 nm.

EXAMPLE 5

Starting diol lactones corresponding to $R^1$ is H or OH may be prepared by hydrolyzing compactin or pravastatin respectively.

What is claimed is:

1. A process for the formation of a compound of formula (I):

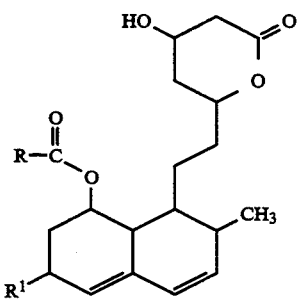

which comprises treating a diol lactone:

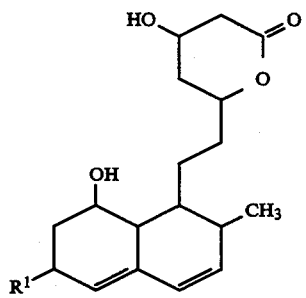

with R—$COOR^2$ in a mixture of a chlorinated hydrocarbon and a hydrocarbon containing an immobilized lipase derived from *Candida cylindracea* ATCC 14830;

wherein
R is 2-butyl,
$R^1$ is $CH_3$, and
$R^2$ is H,
and recovering the compound of formula (I).

2. The process of claim 1 wherein the organic solvent is a 50/50 mixture by volume of chloroform and hexane.

3. A process for the formation of a compound of formula (I):

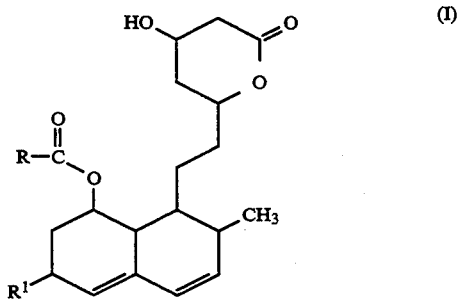

which comprises treating a diol lactone:

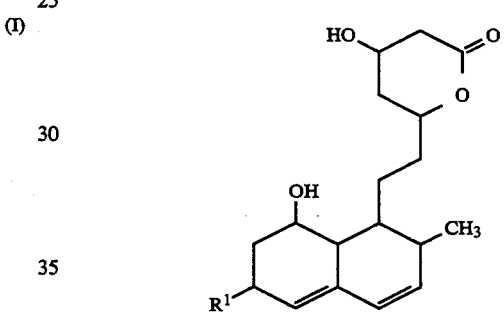

with R—$COOR^2$ in a nonaqueous organic solvent containing lipase Type VII derived from *Candida cylindracea;* wherein R is $C_{1-5}$ alkyl; and
$R^1$ is H, $CH_3$ or OH;
$R^2$ is H or $C_{1-5}$alkyl, and recovering the compound of formula (I).

4. The process of claim 3 wherein the lipase is immobilized.

5. The process of claim 4 wherein the organic solvent is a mixture of a chlorinated hydrocarbon; and a hydrocarbon.

6. The process of claim 4 wherein the organic solvent is a 50/50 volume/volume mixture of chloroform and hexane.

7. The process of claim 5 wherein R is 2-butyl; $R^1$ is $CH_3$ and $R^2$ is H.

* * * * *